(12) United States Patent
Rauchschwalbe

(10) Patent No.: US 6,403,803 B1
(45) Date of Patent: Jun. 11, 2002

(54) BIS(2-CHLOROTHIAZOLYL-5-METHYL) AMINE AND ITS SALTS, AND PROCESS FOR WORKING UP REACTION MIXTURES COMPRISING 5-AMINOMETHYL-2-CHLOROTHIAZOLE AND BIS(2-CHLOROTHIAZOLYL-5-METHYL)AMINE

(75) Inventor: Günter Rauchschwalbe, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/006,539

(22) Filed: Dec. 3, 2001

(30) Foreign Application Priority Data

Dec. 8, 2000 (DE) .......................................... 100 61 083

(51) Int. Cl.$^7$ ............................................ C07D 277/20
(52) U.S. Cl. ...................................................... 548/202
(58) Field of Search .......................................... 548/202

(56) References Cited

U.S. PATENT DOCUMENTS 5,180,833 A   1/1993   Uneme et al. ............... 548/202

FOREIGN PATENT DOCUMENTS

| DE | 196 53 586 | 6/1998 |
| EP | 0 302 389  | 2/1989 |
| EP | 0 763 531  | 3/1997 |

*Primary Examiner*—Joseph K. McKane
*Assistant Examiner*—Rebecca Anderson
(74) *Attorney, Agent, or Firm*—Joseph C. Gil; Richardson E. L. Henderson

(57) ABSTRACT

As a result of a special precipitation, it is possible to work up reaction mixtures containing 5-aminomethyl-2-chlorothiazole and bis(2-chlorothiazolyl-5-methyl)amine in an advantageous manner and to isolate bis(2-chlorothiazolyl-5-methyl)amine or its salts.

11 Claims, No Drawings

BIS(2-CHLOROTHIAZOLYL-5-METHYL) AMINE AND ITS SALTS, AND PROCESS FOR WORKING UP REACTION MIXTURES COMPRISING 5-AMINOMETHYL-2-CHLOROTHIAZOLE AND BIS(2-CHLOROTHIAZOLYL-5-METHYL)AMINE

BACKGROUND OF THE INVENTION

The invention relates to a process for working up reaction mixtures comprising 5-aminomethyl-2-chlorothiazole and bis(2-chlorothiazolyl-5-methyl)amine and further relates to bis(2-chlorothiazolyl-5-methyl)amine and its salts.

5-Aminomethyl-2-chlorothiazole (also called AMCT below) is a precursor for the preparation of insecticides and therefore an industrially important intermediate. From EP-A 446,913 and DE-A 196 53 586, it is known that AMCT can be prepared by reacting 5-chloromethyl-2-chloro-thiazole (also called CCMT below) with ammonia according to the

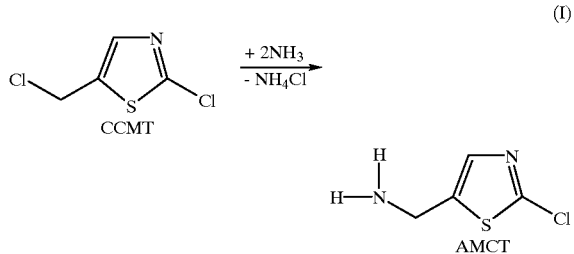

The AMCT is usually separated off from the reaction mixture formed during the conversion by distillation or extraction. In this connection, the multiple pH-controlled extraction with dichloromethane (see examples of DE-A 196 535 86) has proven particularly successful. However, the use of methylene chloride is undesirable on an industrial scale since it is readily volatile and possibly carcinogenic (category C3). Furthermore, an up to six-fold extraction on an industrial scale is associated with considerable expenditure; for reasons of cost and environmental protection, the solvent must be recovered and purified, which in turn is associated with expenditure.

In some instances, the AMCT crude product must, as described in EP-A 446,913, be purified in addition by preparative chromatography. However, the need for preparative chromatography considerably reduces the economic attractiveness of the overall process.

Added to this is the fact that the residues that form during the work-up process of the prior art have not hitherto been passed to a material further processing operation.

The object of the present invention was therefore to provide an improved process for working up reaction mixtures comprising 5-amino-methyl-2-chlorothiazole, which can be obtained by reacting 5-chloro-methyl-2-chlorothiazole with ammonia.

Surprisingly, we have now found that during the reaction of 5-chloromethyl-2-chlorothiazole with ammonia, apart from the desired product AMCT as main by-product, bis(2-chlorothiazolyl-5-methyl)amine (bis-CTMA) of the general formula (II) forms

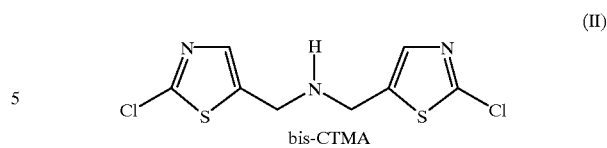

and that a significantly improved work-up of such reaction mixtures is possible by separating this bis-CTMA in the form of its salts.

SUMMARY OF THE INVENTION

The invention provides a process for working up reaction mixtures comprising 5-aminomethyl-2-chlorothiazole and bis(2-chlorothiazolyl-5-methyl)amine obtained by reacting 5-chloromethyl-2-chlorothiazole with ammonia comprising (1) separating off any ammonia present in the reaction mixture,
(2) admixing the resultant reaction mixture with an amount of water and an amount of an inorganic acid HX such that at least 85% of the total amount of the bis(2-chlorothiazolyl-5-methyl)amine salt thereby formed precipitates and at least 85% of the total amount of the 5-aminomethyl-2-chlorothiazole salt thereby formed remains in solution, and
(3) separating off the precipitated bis(2-chlorothiazolyl-5-methyl)amine salt.

The invention further provides bis(2-chlorothiazolyl-5-methyl)amine of the general formula (II)

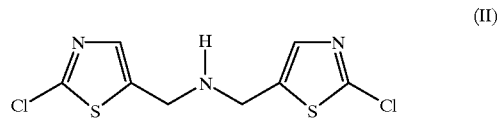

and salts thereof.

In this connection, preference is given primarily to the chloride and the sulfate of bis-CTMA.

DETAILED DESCRIPTION OF THE INVENTION

If the reaction mixture from the preceding conversion of 5-chloro-methyl-2-chlorothiazole with ammonia that is to be used in the process according to the invention still contains excess ammonia, the excess ammonia is first separated from the reaction mixture. This is usually carried out by distillation. In the same way, it is also possible to separate any organic solvent still present in the reaction mixture.

The reaction mixture is then admixed with an amount of water and an amount of an inorganic acid HX such that at least 85% (preferably at least 90%) of the total amount of the secondary ammonium salt of bis-CTMA formed precipitates out, while at least 85% (preferably at least 90%) of the total amount of the primary ammonium salt of AMCT formed remain in solution.

As inorganic acid HX, it is possible to use, for example, HCl, $H_2SO_4$, $H_3PO_4$, or HBr, preference being given to using HCl or $H_2SO_4$. The inorganic acid is expediently used in the form of aqueous solutions of customary concentrations that either are available commercially or else can be readily prepared by dilution of a concentrated form.

The required amount of water and the required amount of acid can be easily determined by the person skilled in the art.

Preferably, a total amount of water (i.e., including the water that enters into the reaction mixture via the inorganic acid used) of 60 to 200 ml(preferably 100 to 150 ml of water) is added to the reaction mixture per mole of CCMT, or 55 to 180 ml (preferably 90 to 135 ml) of water, based on the total molar amount of amino thiazoles AMCT and bis-CTMA formed.

It is also possible to carry out the process using an up to 30% molar strength deficit or excess of the inorganic acid, based on the total amount of amino thiazoles AMCT and bis-CTMA formed. Preference is given to carrying out the process using 80 to 100 molar % of inorganic acid, based on the total amount of amino thiazoles AMCT and bis-CTMA formed. In this connection, a pH of 0 to 3 (preferably of 1 to 2) is set. As the reaction temperature, a temperature in the range from 10 to 40° C. (preferably 25 to 30° C.) has proven successful.

During the stirring of the reaction mixture, the salts of the amines AMCT and bis-CTMA form; in the case of the preferred use of HCl, the hydrochloride forms. Here, at least 85% (preferably at least 90%) of the secondary ammonium salt formed precipitates out, while at least 85% (preferably at least 90%) of the primary ammonium salt remains in the mother liquor in high purity, as determined by HPLC.

The solubilities of the ammonium salts of AMCT and bis-CTMA can be influenced within certain limits by adjusting the pH, by adding salts (such as, for example, NaCl or NH$_4$Cl) or else by adjusting the temperature. Such methods of adjusting solubility are familiar to the average person skilled in the art. In particular, the addition of NaCl in an amount of 10% by weight of the total water phase has proven successful.

The precipitated-out ammonium salt of bis-CTMA can be separated from the reaction mixture virtually completely by filtration, centrifugation, or other mechanical separation methods. The losses of AMCT during this separation are very low and do not impair the economic feasibility of the process.

The salt of bis-CTMA obtained during the separation as residue can be after-washed, for example, with water, dilute hydrochloric acid, NaCl solution, or NH$_4$Cl solution. The washing solutions that form in the process can be combined with the reaction mixture that has been freed from the bis-CTMA and that contains the AMCT in order to obtain an optimum AMCT yield. Should an even more extensive purification of the bis-CTMA be desired, this is possible, for example, by extraction, chromatography, crystallization, or recrystallization.

An acidic, aqueous solution of the ammonium salt of AMCT is obtained, which can either be further used directly in the next reaction stage or else can be further purified and isolated by known methods (such as evaporation and subsequent recrystallization or extraction, or purification by adsorption etc.). Such a purification is preferred if it is desirable to obtain a product of AMCT that is largely free from inorganic salts or if it is not the salt, but the free base AMCT that is desired.

This varying behavior in the solubility of the ammonium salts of AMCT and bis-CTMA is hitherto unknown, could not have been foreseen, and permits an advantageous work-up of the reaction mixtures used. Using the process according to the invention, bis-CTMA has been found and isolated for the first time.

Bis(2-chlorothiazolyl-5-methyl)amine and its salts, particularly the HCl salt and the hydrate of this HCl salt, can be used as intermediate for the preparation of crop protection compositions, of pharmaceuticals, and of textile dyes.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1

19 g of water and 204 g (335 ml; 12.0 mol) of ammonia were introduced into an autoclave and heated to 50° C. Over the course of about 1 hour, a solution of 51.5 g of CCMT (98% strength; 0.30 mol) in 10 g of methyl tert-butyl ether (MtBE) was pumped in, and the pump was rinsed with about 52 g (70 ml) of MtBE. The mixture was after-stirred for 1 hour; the internal pressure reached a maximum of 20 bar during this stirring. The mixture was cooled to RT and the system was slowly decompressed. The autoclave contents (86 g, two-phase) were removed, and residual NH$_3$ and MtBE were distilled off in an aspirator vacuum at 22° C. The mixture was firstly diluted with 8 ml of water and then acidified with 20 ml (23.5 g; 0.24 mol) of concentrated HCl to a pH of 1. A further 9 ml of water were added, giving 106.8 g of solution (B1/1). Upon standing, white crystals precipitated after 1 to 2 hours at 25° C. The crystals were filtered off and washed with 2×10 ml of ice water, giving 11.6 g (moist) or 8.1 g of B1/dr. (i.e., dry) solid, and 84.3 g of solution (B1/ML), and 12.5 g of wash water 1 (B1/W1) and 13.0 g of wash water 2 (B1/W2).

The content of AMCT and bis-CTMA in the various stages was determined by HPLC with an accuracy of about 1% in each case and is given in Table 1 below.

TABLE 1

| Example 1 | Final weight [g] | AMCT content [%] | AMCT content [g] | bis-CTMA content [%] | bis-CTMA content [g] | Yield AMCT [% of theory] | Yield bis-CTMA [% of theory] |
|---|---|---|---|---|---|---|---|
| B1/1 | 106.8 | 33.8 | 36.1 | 3.2 | 3.4 | 81.0 | 8.1 |
| B1/dr. | 8.1 | 43.8 | 3.6 | 33.3 | 2.7 | 8.0 | 6.4 |
| B1/ML | 84.3 | 34.5 | 29.1 | 0.2 | 0.2 | 65.2 | 0.4 |
| B1/W1 | 12.5 | 20.0 | 2.5 | 1.5 | 0.2 | 5.6 | 0.4 |
| B1/W2 | 13.0 | 12.6 | 1.6 | 2.2 | 0.3 | 3.7 | 0.7 |
| Product: Sum: ML + W1 + W2 | 109.8 | 29.6 | 32.5 | 0.55 | 0.55 | 72.9 | 1.3 |

Example 2

The procedure was analogous to Example 1 but used twice the amount of feed material and after-washing was carried out with concentrated NaCl solution instead of with water.

TABLE 2

| Example 2 | Final weight [g] | AMCT content [%] | [g] | bis-CTMA content [%] | [g] | Yield AMCT [% of theory] | bis-CTMA [% of theory] |
|---|---|---|---|---|---|---|---|
| B2/ML | 169.2 | 36.2 | 61.3 | 0.2 | 0.3 | 68.7 | 0.3 |
| B2/W1 | 19.8 | 24.3 | 4.8 | <0.1 | <0.01 | 5.4 | |
| B2/W2 | 21.3 | 4.7 | 1.0 | <<0.1 | <0.01 | 1.1 | |
| Sum: ML + W1 + W2 | 210.3 | 31.5 | | 0.14 | | 74.3 | 0.2 |

As can be seen, for this type of after-washing with NaCl solution, the content of bis-CTMA in the fractions that comprise the desired AMCT was even lower, and even better removal of bis-CTMA and higher purity of AMCT was therefore possible.

This gave AMCT as aqueous solution in hydrochloric acid that, according to HPLC, had a purity of 99% (assessment as the sum of the % areas at a detector wavelength of 226 nm).

Example 3

Synthesis of bis(2-Chlorothiazolyl-5-methyl)amine and Analytical Characterization 17 g of 2-chloro-5-chloromethylthiazole (0.1 mol) were dissolved in 3 g of DMF and admixed with 135 g of 26% strength $NH_3$ solution (2 mol). The mixture was left to stand for 6 days at RT. During this time, two phases formed. The mixture was diluted with 50 ml of water, acidified with HCl (37%) (pH 1) and heated to 55° C., during which white crystals that precipitated from time to time redissolved. Following clarification with activated carbon, the product crystallized out upon cooling into white crystals, which were filtered off, washed with ice water, and dried at 50° C. under reduced pressure. The yield was 5.6 g (according to CHN analysis 88.5% free base or 100% HCl salt) and corresponded to 0.0178 mol (35.6% of theory). Upon prolonged standing in air, the product drew in water and formed a monohydrate.

Furthermore, the structure was produced by MS: m/z 279/281/283, M+, 2 Cl; <1%; 244/246,1 Cl, M—Cl, 8%; 132/134, 1 Cl, 100%. (When using chemical ionization, the peak at 280/282/284 (M+1) was found as base-peak.) 1H-NMR (DMSO): δ 3.43 (s, br., 2H, $H_2O$); 4.44 (s, 4H, —$CH_2$—N); 7.85 (s, 2 H, =CH—); 10.42(s, br., 2 H, $NH_2$). (Here, br means broad signal; s means singlet).

In chromatographic analysis (HPLC), the retention time was identical in that of the product that had been separated off according to Example 1 or by filtration.

What is claimed is:

1. A process for working up reaction mixtures comprising 5-aminomethyl-2-chlorothiazole and bis(2-chlorothiazolyl-5-methyl)amine obtained by reacting 5-chloromethyl-2-chlorothiazole with ammonia comprising (1) separating off any ammonia present in the reaction mixture,
    (2) admixing the resultant reaction mixture with an amount of water and an amount of an inorganic acid HX such that at least 85% of the total amount of the bis(2-chlorothiazolyl-5-methyl)amine salt thereby formed precipitates out and at least 85% of the total amount of the 5-aminomethyl-2-chlorothiazole salt thereby formed remains in solution, and
    (3) separating off the precipitated-out bis(2-chlorothiazolyl-5-methyl)amine salt.

2. A process according to claim 1 wherein the inorganic acid HX used is HCl, $H_2SO_4$, $H_3PO_4$, or HBr.

3. A process according to claim 1 wherein the reaction mixture is admixed with an amount of water and an amount of inorganic acid HX such that at least 90% of the total amount of the bis(2-chlorothiazolyl-5-methyl)amine salt thereby formed precipitates out and at least 90% of the total amount of the 5-aminomethyl-2-chlorothiazole salt thereby formed remains in solution.

4. A process according to claim 1 wherein a total of 60 to 200 ml of water is added to the reaction mixture per mole of 5-chloromethyl-2-chlorothiazole.

5. A process according to claim 1 wherein a total of 55 to 180 ml of water is added to the reaction mixture based on the total molar amount of 5-aminomethyl-2-chlorothiazole and bis(2-chlorothiazolyl-5-methyl)amine formed.

6. A process according to claim 1 carried out using an up to 30% strength by weight deficit or excess of the inorganic acid, based on the total amount of amino thiazoles 5-aminomethyl-2-chlorothiazole and bis(2-chlorothiazolyl-5-methyl)amine formed.

7. A process according to claim 1 wherein a pH of 0 to 3 is set.

8. A process according to claim 1 carried out at a reaction temperature in the range from 10 to 40° C.

9. A process according to claim I wherein in step (2), a salt is added to the reaction mixture.

10. A process according to claim 1 wherein the bis(2-chloro-thiazolyl-5-methyl)amine salt obtained after separation in step (3) is after-washed with water, a dilute hydrochloric acid, a NaCl solution, or a $NH_4Cl$ solution.

11. Bis(2-chlorothiazolyl-5-methyl)amine of the formula

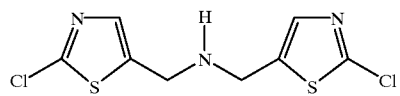

or a salt thereof.